(12) United States Patent
Proxenos et al.

(10) Patent No.: US 12,036,376 B2
(45) Date of Patent: Jul. 16, 2024

(54) AIRWAY DILATION DEVICE AND ASSOCIATED METHOD OF DEPLOYMENT

(71) Applicant: MINOAN MEDICAL (PTY) LIMITED, Johannesburg (ZA)

(72) Inventors: Matthew Ryece Proxenos, Johannesburg (ZA); Kenneth Stuart Park, Constantia (ZA); Markus Lehmann, Munich (DE); Gregory Vizirgianakis, Johannesburg (ZA); Darlene Elizabeth Lubbe, Cape Town (ZA); Debbie Lee Lloyd, Cape Town (ZA)

(73) Assignee: MEDINOTEC, INC., Las Vegas, NV (US)

(*) Notice: Subject to any disclaimer, the term of this patent is extended or adjusted under 35 U.S.C. 154(b) by 566 days.

(21) Appl. No.: 16/860,596

(22) Filed: Apr. 28, 2020

(65) Prior Publication Data

US 2020/0254229 A1 Aug. 13, 2020

Related U.S. Application Data

(63) Continuation of application No. PCT/ZA2018/050066, filed on Dec. 12, 2018.

(30) Foreign Application Priority Data

Feb. 5, 2018 (ZA) .................................. 201800810

(51) Int. Cl.
*A61M 29/00* (2006.01)
*A61M 25/10* (2013.01)
*A61M 25/00* (2006.01)

(52) U.S. Cl.
CPC ........ *A61M 29/00* (2013.01); *A61M 25/1002* (2013.01); *A61M 25/1011* (2013.01);
(Continued)

(58) Field of Classification Search
CPC .............. A61M 29/00; A61M 25/1002; A61M 25/1011; A61M 2025/0004;
(Continued)

(56) References Cited

U.S. PATENT DOCUMENTS

2004/0064150 A1* 4/2004 Becker ............ A61M 25/10181
606/196
2007/0213661 A1* 9/2007 Gobel ................... A61F 2/0013
604/96.01
(Continued)

FOREIGN PATENT DOCUMENTS

WO 2012/009486 A2 1/2012
WO 2012/099979 A1 7/2012
(Continued)

OTHER PUBLICATIONS

Brazillian Examination Report dated Dec. 12, 2018; Appln. No. BR112020015833-0.
(Continued)

*Primary Examiner* — Richard G Louis

(57) ABSTRACT

This invention relates to an airway dilation device comprising a catheter; an inflation tube within the catheter, and having a lumen defined by its inner wall; a duct within the catheter, for the insufflation of a fluid, the duct being sealed against any fluid flow between it and the tube; a cluster of balloons, arranged about the catheter, the balloons being manipulated between a stowed condition, in which the balloons are deflated, and a deployed condition, in which the balloons are inflated; and inflating means, for inflating the balloons; characterised in that, when stowed, each balloon is folded and staggered relative to each adjacent balloon, and such that continuous insufflation remains possible, even when deployed. This invention relates, further, to corresponding methods of deployment of devices.

38 Claims, 6 Drawing Sheets

(52) U.S. Cl.
CPC ............ *A61M 2025/0004* (2013.01); *A61M 2025/0008* (2013.01); *A61M 2025/0039* (2013.01); *A61M 2025/0057* (2013.01); *A61M 2202/0208* (2013.01); *A61M 2202/0241* (2013.01); *A61M 2205/07* (2013.01); *A61M 2210/1046* (2013.01)

(58) Field of Classification Search
CPC .. A61M 2025/0008; A61M 2025/0039; A61M 2025/0057; A61M 2202/0208; A61M 2202/0241; A61M 2205/07; A61M 2210/1046; A61M 16/0409; A61M 2025/1097; A61M 16/04; A61M 16/0438; A61M 16/0486; A61M 25/0043; A61M 25/1025; A61M 2025/0059; A61M 2025/1013; A61M 2210/0618; A61M 2210/065; A61M 29/02; A61M 25/1018; Y02T 10/12; Y10S 55/14; F01N 3/00
See application file for complete search history.

(56) References Cited

U.S. PATENT DOCUMENTS

| | | | | |
|---|---|---|---|---|
| 2007/0260177 | A1* | 11/2007 | Warnack | A61M 25/10 604/96.01 |
| 2009/0032121 | A1* | 2/2009 | Chon | F16K 17/30 606/107 |
| 2010/0056999 | A1* | 3/2010 | Herrera Cedeno | A61M 25/04 604/103.01 |
| 2010/0087781 | A1 | 4/2010 | Adams et al. | |
| 2010/0087881 | A1* | 4/2010 | Shuros | A61N 1/3684 607/4 |
| 2011/0144742 | A1* | 6/2011 | Madrid | A61F 2/2433 623/2.11 |
| 2013/0150881 | A1 | 6/2013 | Wang et al. | |
| 2013/0190796 | A1* | 7/2013 | Tilson | B29C 70/549 606/192 |
| 2015/0272732 | A1 | 10/2015 | Tilson et al. | |
| 2017/0252543 | A1* | 9/2017 | Gomes | A61M 25/1002 |
| 2017/0252544 | A1 | 9/2017 | Gomes et al. | |

FOREIGN PATENT DOCUMENTS

| | | |
|---|---|---|
| WO | 2014/030078 A1 | 2/2014 |
| WO | 2017/078733 A1 | 5/2017 |

OTHER PUBLICATIONS

Written Opinion and Supplement European Search Report; Nov. 4, 2021 (Search completed Oct. 25, 2021); Appln. No. EP 18 90 3920.
International Search Report mailed Apr. 17, 2019; PCT/ZA2018/050066.
International Preliminary Report on Patentability completed Feb. 27, 2020.
Written Opinion of the International Searching Authority mailed Apr. 17, 2019; PCT/ZA2018/050066.
EPO Communication dated Jan. 31, 2023; Appln. 18903920.9.
Korean Intellectual Property Office Written Opinion; Appln. No. 10-2020-7025649; dated Mar. 21, 2023.
Korean Notice of Allowance; Application 10-2020-7025649; dated Nov. 29, 2023.

* cited by examiner

FIGURE 1.1
BOSTON SCIENTIFIC SCIMD, INC. (US 2013/0150881)

FIGURE 1.2
LOMA VISTA MEDICAL, INC. (WO 2012/099979)

AIRWAY DILATION DEVICE AND ASSOCIATED METHOD OF DEPLOYMENT

FIELD OF THE INVENTION

THIS INVENTION relates, broadly, to an airway dilation device. It extends, too, to an associated method of deployment of the device in vivo.

BACKGROUND TO THE INVENTION

A number of different stent- and catheter-type devices are well-known and are used to reduce narrowing and/or remove blockages in arteries, veins, air passages and the lumens of organs in the body. It is stressed however, that the present invention is intended to be applied exclusively to the passageways of the respiratory airway (being the nasal cavity, nasopharynx, pharynx, larynx, trachea and bronchi) and the digestive tract (for present purposes: being the pharynx and oesophagus).

In cases of medical need in which a patient exhibits an obstructed or occluded air passageway, balloon dilation has been used to widen the narrowing, allowing the patient to breathe and preventing asphyxiation. In emergency cases, drastic medical intervention is often called for. Typically, such measures are extremely dangerous and invasive—for example: a tracheotomy, cricothyrotomy and/or endotracheal intubation. Such procedures are dangerous, not only when they are undertaken, but again when the medical devices are removed from the patient, once stabilised. The extent of scarring, damage, iatrogenic throat or airway trauma that is inflicted by such measures is also regarded as undesirable. These immediate life-saving interventions often lead to patients having life-long tracheostomies, permanent stenting of the airway or major surgery later in life to resect the damaged part of the airway. An emergency tracheotomy or cricothyrotomy can also complicate long-term management and compromise the success of a future tracheal resection.

It will also be appreciated that forming a stoma in a tracheal wall will result in unavoidable tissue damage and thus scar tissue which, again, is both dangerous and undesirable. Other medical procedures, such as the insertion of endotracheal tubes (intubation), have been known to result in conditions such as acquired tracheal or subglottic stenosis—the friction and/or pressure inherent in such procedures, if prolonged or improperly performed, can result in the interruption of blood flow to sensitive mucosa, leading to necrosis. Resultant scarring has also been Known to lead to stenosis.

In recent times, various balloon catheters have been conceived in an effort to treat the condition. However, these are not without their difficulties. For example: traditional balloon catheters tend to be too short to fit through a traditional, rigid bronchoscope. As a result, such balloons require suspension laryngoscopy, rendering the patient apnoeic during the procedure, making surgery very dangerous. Moreover, traditional balloon catheters tend to be occlusive during inflation. This causes very quick desaturation as little to no gasses can be delivered to the patient. Furthermore, it is often the case that traditional balloon catheters are not sufficiently rigid to force such balloons at least partially through a small tracheal stenosis. Elaborating on this point: many traditional balloon catheters are limited by the maximum pressure that can be provided to dilate strictures. It has been noted that these balloons are capable of operation only at relatively low pressures (typically: no more than 3-6 bar). This is often too low to be effective in relieving blockages in severe cases.

Yet a further disadvantage associated with the prior art solutions is that the shape and orientation of the balloon elements is sub-optimal and awkward to manipulate in vivo, making insertion and/or extraction from the body difficult and, in some cases, traumatic.

The inventors are aware of two prior art balloon-bearing dilation devices in particular, namely those proprietary to the Boston Scientific Corporation (as described in US patent no. 2013/0150881) and Loma Vista Medical, Inc., a subsidiary of CR Bard, Inc. (as described in PCT patent application no. WO 2012/099979). The former has exclusive application to valvuloplasty procedures, which is outside of the scope of the present invention and, in any event, differs in structure and operation. The latter is described in detail in the context of inflation of the aortic valve (notably at pages 40-41 of the PCT patent specification). This is unsurprising, given the relative arrangement of the series of balloons in each case. The invention described in WO 2012/099979 suffers from another shortcoming, in that the balloon arrangement is necessarily encircled in a shell (perhaps best illustrated in FIGS. 23A, 24A, 23B & 24B), which adds further to the overall thickness of that dilation device—this is regarded as disadvantageous. It will be appreciated by the expert in the field that these devices are relatively large and voluminous in their deployed state, and suitable for deployment only in (relatively) larger structures—such as the aorta. Consequently, they are too large for application in relatively confined spaces, such as the airway. In other words, it will be appreciated by the expert in the field that it is disadvantageous for a dilation device to be excessively thick because it will be difficult for the device to pass through a tight narrowing.

Further, still: another disadvantage associated with known solutions is that traditional occlusive balloons do not allow simultaneous ventilation or gaseous anaesthesia during inflation. As a result, during the process of inflation of these balloons, oxygen saturation rapidly reduces to unhealthy levels, carbon dioxide levels build up, posing a risk of neurological damage. Further, the attending anaesthetist may be unable to deliver gasses necessary for appropriate levels of anaesthesia—it will be appreciated that this creates a considerable risk to patient health. As a consequence of this limitation, these prior art balloons are inflated only for short periods of time before being deflated and withdrawn, so as to allow ventilation and anaesthesia delivery. The procedure therefore needs to be repeated several times in order to achieve complete dilation—this, too, is regarded as disadvantageous.

Finally, for purposes of the present specification, the term "cone" is used in reference to the specific, narrow portion of each balloon, which appears on either end of the barrel section. The cones are marked in the accompanying Figures by reference numeral 140—notwithstanding the name "cone", these structures need not necessarily be conical in shape. In addition, for purposes of the present specification, the term "tail" is used in reference to the specific tube, or tube-like structure that transitions from each cone, on the opposite ends of the barrel. The tails are marked in the accompanying Figures by reference numerals 130 (for proximal tails) and 150 (for distal tails). Correspondingly, reference numeral 140 is used to denote each proximal cone, and reference numeral 170 is used to denote each distal cone. The terms "cone" and "tail" are both well understood in the art.

OBJECT OF THE INVENTION

It is an object of the present invention to provide an airway dilation device, and an associated method of deployment, that will overcome, at least partially, the disadvantages described above.

SUMMARY OF THE INVENTION

According to a first aspect of the invention, there is provided an airway dilation device comprising:
- a catheter, being dimensioned and configured for insertion at least partially into an airway, the catheter having an inflating end, and a distal end;
- a continuous inflation tube, being housed substantially concentrically within the catheter, the inflation tube having a lumen defined by its inner wall, and terminating in the same inflating end as the catheter;
- a duct, for the insufflation of a fluid, the duct also being housed substantially concentrically within the catheter, and bounded by the inflation tube along at least some of the length thereof, the duct being sealed hermetically against any fluid flow communication between it and the inflation tube;
- a cluster of balloons, arranged in a substantially circular arrangement about the wall of the catheter, the balloons being manipulated selectively between a stowed condition, in which the balloons are deflated, and a deployed condition, in which the balloons are inflated; and
- inflating means, for inflating the balloons;
  - characterised, first, in that, when in the stowed condition, each balloon is folded and staggered relative to each adjacent balloon, to prevent a substantial overlay between pairs of balloons, so as to achieve an optimal, smallest diameter of the complete cluster of balloons and characterised, second, in that continuous insufflation remains possible, even when the balloons are in their deployed condition.

Each balloon may be bonded to each adjoining balloon in the cluster, along at least one edge.

The cluster of balloons may be affixed securely to the wall of the catheter, along at least some portion thereof, and held fast, so as to prevent separation of the cluster from the catheter.

Each balloon may further include a cone formation and a tail formation on each end of each respective balloon, being the proximal end and the distal end.

Preferably, each distal tail is affixed securely to the wall of the catheter, along at least some portion thereof, and held fast, so as to restrict movement of the balloons to positioning between the stowed condition and the deployed condition only.

Each of the proximal tails of each balloon may take the form of an inflationary tube for its associated balloon.

The device may further include a film layer, for providing additional support to the cluster of balloons.

Preferably, the film layer follows, at least partially, the contours of at least some of the balloons in the cluster.

Preferably, the film layer is bonded to at least part of at least some of the balloons in the cluster.

The film layer may be bonded to the inner surface of the balloons.

The film may be made of a material selected from the group consisting of: polyethylene terephthalate, poly(ether-block-amide), polyamide, polyurethane, and a combination of these.

The series of proximal tails may extend through a common opening into the inflation tube, the common opening being sealed to prevent the escape of inflating fluid into the duct, alternatively into the airway, further alternatively into both the duct and the airway.

The series of distal tails of each balloon may terminate in a common distal tip, the distal tip sealing the balloon arrangement hermetically, to as to facilitate pressurisation of the cluster on inflation, and to prevent the escape of inflating fluid into the airway.

The proximal cone and the distal cone of any two adjacent balloons may be arranged relative to each other so as never to overlap, thus ensuring that any one balloon is staggered relative to each adjacent balloon.

Each balloon may include a central barrel portion. Preferably, when the balloon is in a deployed condition, the barrel portion is substantially circular in cross-section.

The inflating means may comprise an inflating port located on the catheter, the inflating port being dimensioned and configured to engage an external source of pressurised fluid for inflating the balloons, the inflationary port being in fluid flow communication with each proximal tail.

The device may further comprise a secondary port, located at the inflating end of the catheter, alternatively along the length of the catheter, the secondary port opening into the duct, for insufflation of a medicament.

The medicament may be selected from the group consisting of: air, oxygen, anaesthesia, topical drugs, and a combination of these.

The secondary port may further be used to provide jet insufflation of oxygen, alternatively to facilitate manoeuvring of a laser fibre through the airway into position.

The duct may be dimensioned and configured to facilitate manoeuvring of a secondary medical tool therethrough.

The secondary medical tool may be selected from the group consisting of: a guidewire, a laser fibre, a tracheal stent, and a combination of these.

The catheter may be dimensioned and configured for insertion and delivery in and through a device selected from the group consisting of: a conventional rigid bronchoscope, a conventional laryngoscope, an endotracheal tube, a tracheostomy tube, supraglottic airway device, nasopharyngeal tube and laryngeal mask airway.

At least some balloons may be coated in a medicinal compound, the medicinal compound being dispersed on inflation of the balloons.

The device may further comprise at least one visual indicator, for indicating the position of the cluster under direct inspection, alternatively under x-ray inspection.

The device may further comprise a check-valve for dissipating excess pressure. Preferably, the check-valve comprises a stopper and spring arrangement, the spring being biased towards a loaded position in which the stopper is held fast, and characterised in that the spring is movable towards a sprung condition, when the fluid pressure within the lumen exceeds a predetermined value, thus forcing the stopper to open, and vent the fluid.

The device may comprise at least two balloons. Preferably, the device comprises between 5-12 balloons in a cluster.

Each balloon may have a wall thickness of between 8 μm to 60 μm, and preferably between 20 μm to 33 μm—suitable for an adult—and between 10 μm to 20 μm—suitable for a child.

The wall thickness of any balloon may vary at different points along its length. Preferably, the wall thickness of a balloon is relatively thicker on either cone and tail, and at its thinnest in the barrel portion.

Each balloon may be capable of maintaining substantially complete inflation at pressures of between 4 bar to 24 bar, preferably between 4 bar to 16 bar, and most preferably between 6 bar to 14 bar.

The inflating fluid may be selected from the group consisting of: air, sterile water, saline, a contrast medium fluid, and a combination of these According to a second aspect of the invention, there is provided a method of deployment of an airway dilation device, the method comprising the steps of:
providing an airway dilation device in accordance with the first aspect of this invention;
inserting the airway dilation device into an airway;
manipulating the distal end of the catheter proximate the site of airway constriction; and
actuating the inflating means to inflate the balloons, thus compelling dilation of the airway.

The device may be inserted into an airway via a manoeuvring guide.

The manoeuvring guide may be selected from the group consisting of: a bronchoscope, a laryngoscope, an endotracheal tube, a tracheostomy tube, supraglottic airway device, nasopharyngeal tube and a laryngeal mask airway.

Preferably, the device is inserted into the body under endoscopic visualisation.

The method may further comprise the step of inserting a secondary medical tool, into the duct.

The secondary medical tool may be selected from the group consisting of: a guiding wire, a laser fibre, a tracheal stent, and a combination of these.

BRIEF DESCRIPTION OF THE DRAWINGS

In order to describe the invention, embodiments thereof are described hereunder, purely as examples, without limiting the scope of the invention, wherein.

DETAILED DESCRIPTION OF THE DRAWINGS

Figure 1:
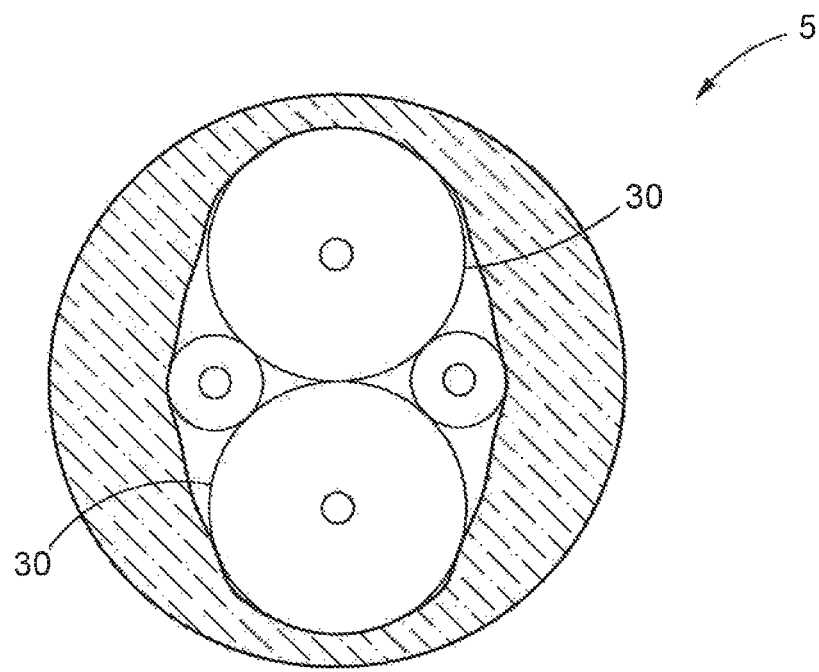
FIG. 1 depicts a cross section through two typical balloon-based dilators disclosed in the prior art.
Figure 1:
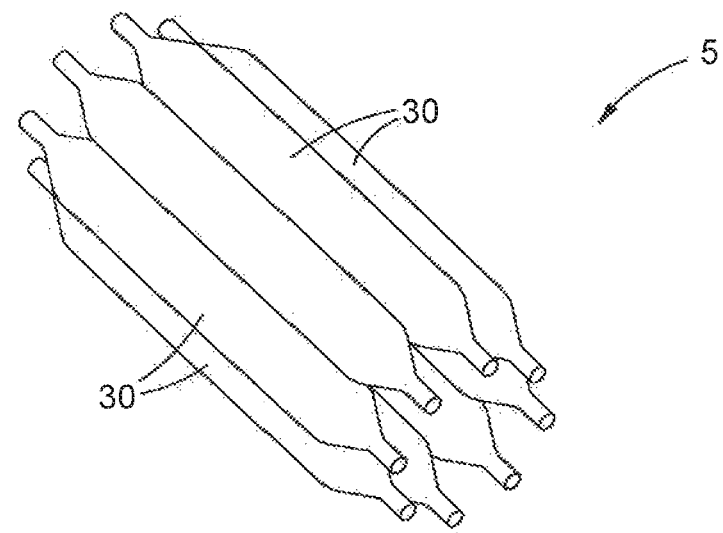

Before describing the invention, reference is made, first, to FIG. 1, which depicts two typical dilation devices (5) that are known in the prior art. Attention is drawn to the series of balloons (30) in each of these devices (5). It will be noted that the balloons are aligned shoulder-to-shoulder (as in FIG. 1.1) or aligned in parallel, such that the balloons (30) overlap (as in FIG. 1.2). It will be appreciated by the expert in the field that neither of these arrangements is optimal, for purposes of maximising structural packing density of the balloons (30) within the devices (5). As a result, the devices (5) are relatively bulky and large.

Figure 4:
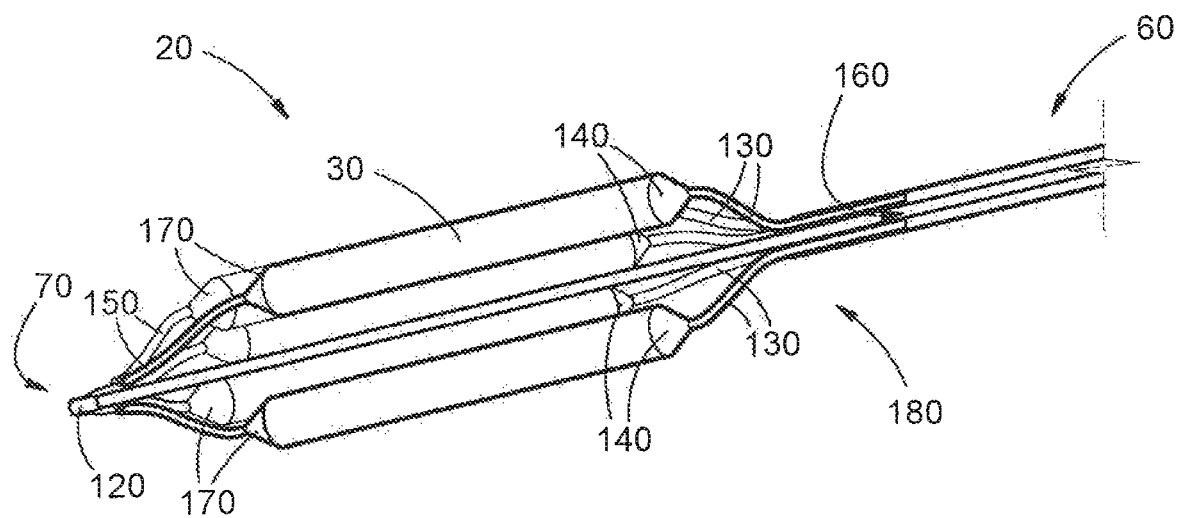
FIG. 4 depicts a longitudinal, cross-sectional view of the device depicted in FIG. 3.
Figure 5:
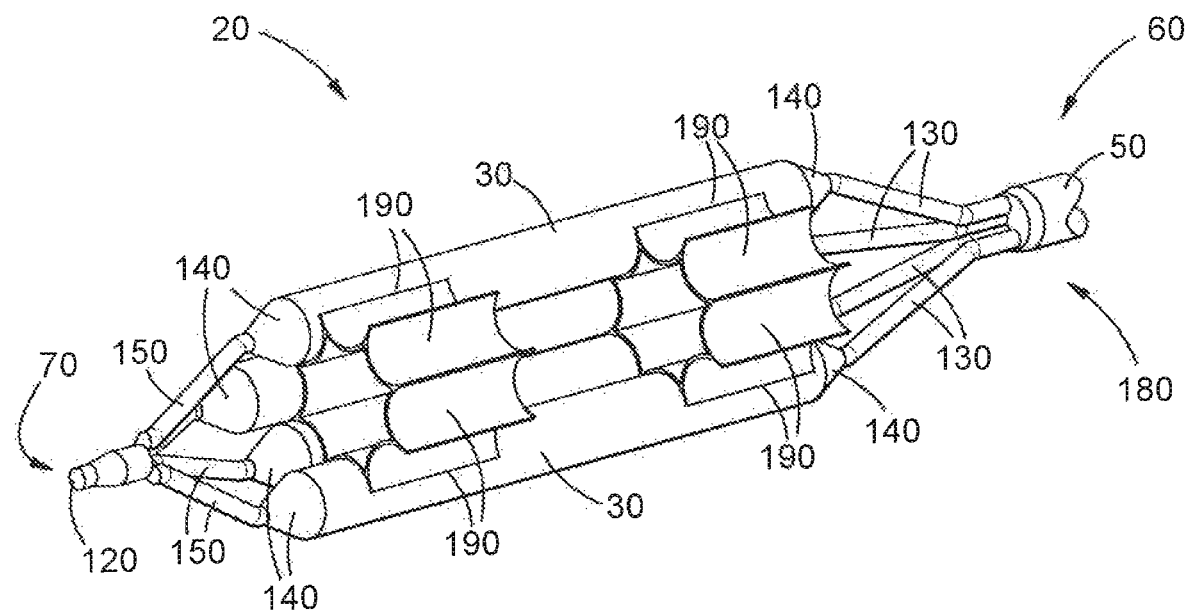
FIG. 5 depicts the longitudinal, isometric view illustrated in FIG. 4, but with some balloons hidden (in partial cutaway) in order to highlight the film layer in the cluster sub-assembly.
Figure 6:
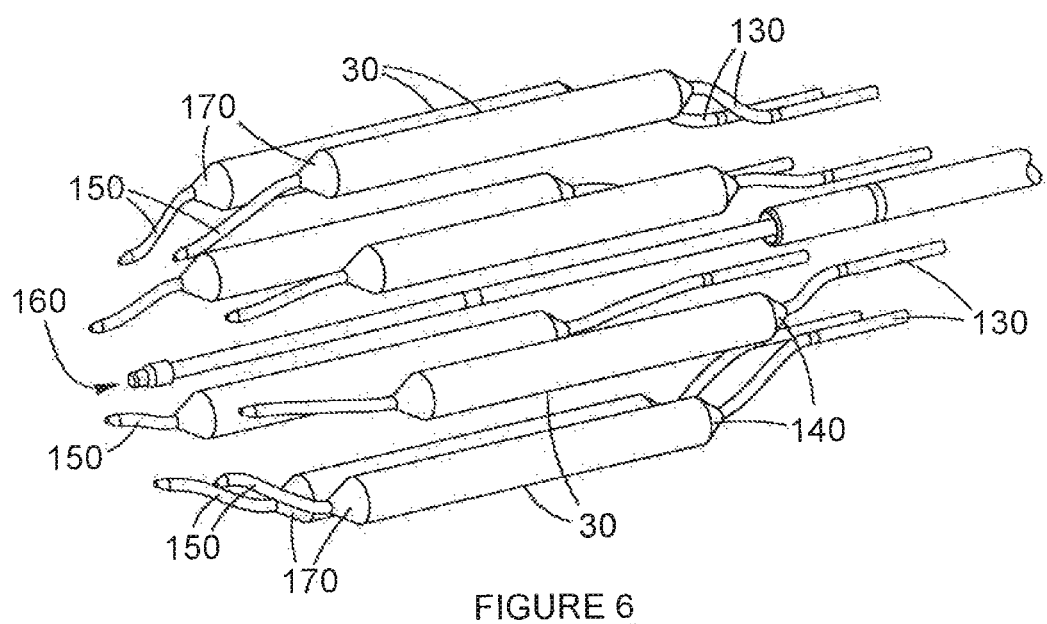
FIG. 6 depicts an exploded, isometric view of much of the detail depicted in FIG. 3.
Figure 9A:
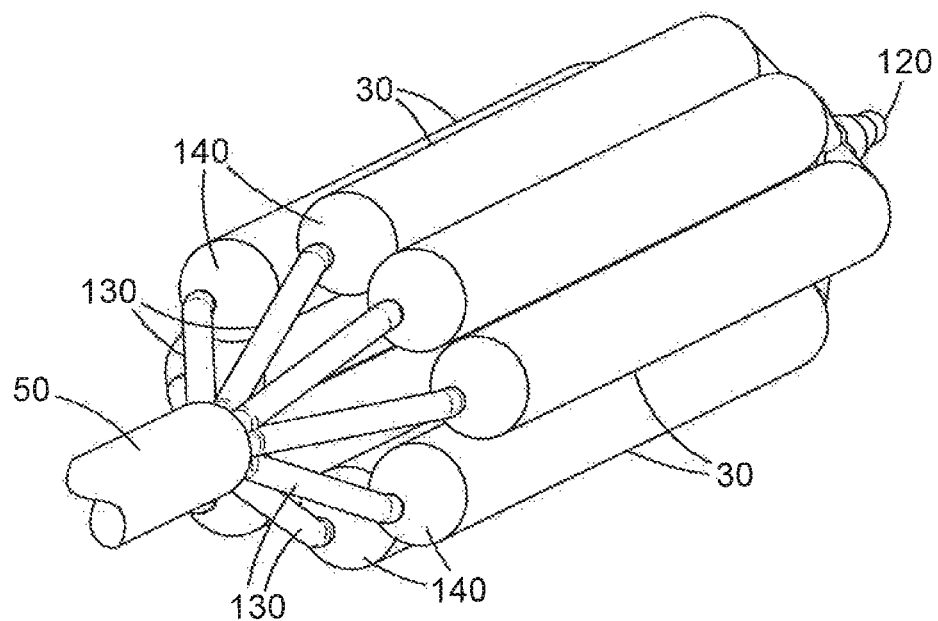
FIG. 9a depicts an isometric view of a close-up of a portion of the device depicted in FIG. 2, along the line A-A, as viewed from the inflating end of the catheter.
Figure 9B:
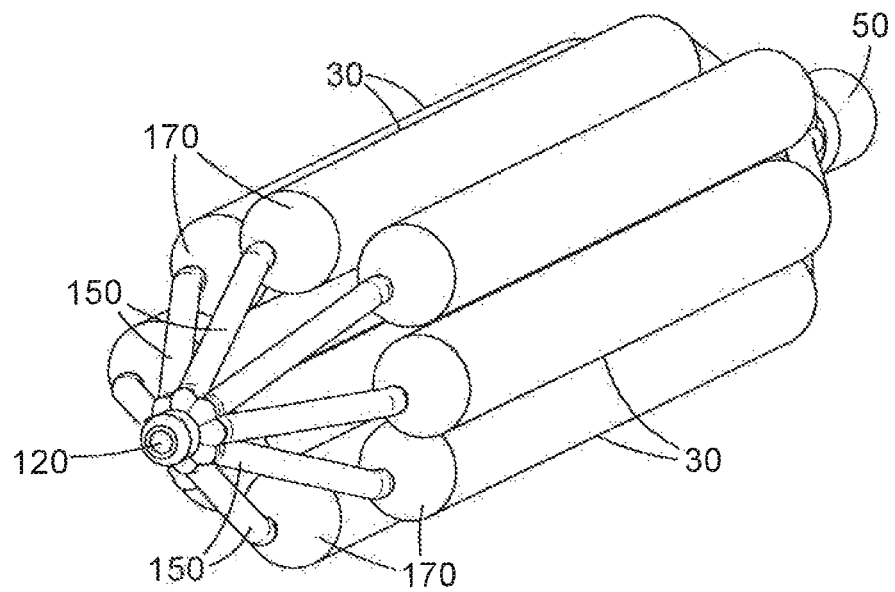
FIG. 9b depicts an isometric view of a close-up of a portion of the device depicted in FIG. 2, along the line A-A, as viewed from the distal tip.
Figure 10:
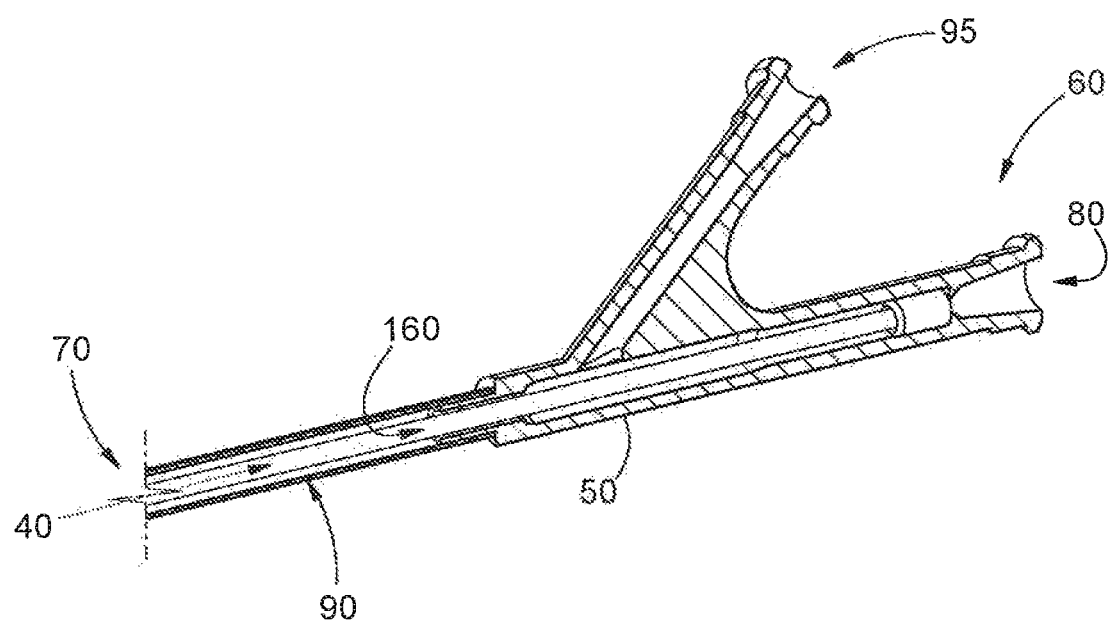
FIG. 10 depicts a longitudinal cross section through the device depicted in FIG. 2, along line C-C, emphasising the inflation tube, lumen and duct.

Referring now to FIGS. 2-10, which depict preferred embodiments of the invention, an airway dilation device, is disclosed and is referred to generally by numeral 20, The corresponding methods for the deployment of the device (20) are also disclosed. However, neither method is depicted specifically in the figures, although the steps involved are inferred from both the Figures and the description provided here. The device (20) comprises a catheter (50), the elongate shape of which facilitates ready insertion into an airway (not depicted). The catheter (50) terminates at two ends, namely: its inflating end (60) and its distal end (70). Situated internally of the catheter (50), and substantially concentrically, is inflation tube (90), which terminates at the same inflating end (60), A duct (160), which is used to achieve the insufflation of fluid, is also housed substantially concentrically within the catheter (50), the duct (160) being bounded by the inflation tube (90) along its length—this is best depicted in FIGS. 6 and 9. The duct (160) is sealed hermetically against any fluid flow communication between it (the duct (160)) and the inflation tube (90). In the interests of absolute clarity, it is stressed that, the lumen (40) actually runs through duct (160)—this is because of the relative arrangement of the inflation tube (90) and duct (160)—in particular: inflation tube (90) surrounds the duct (160). This can be seen from the axial cross-section shown in FIG. 6: in it, the inflation tube (90) appears as the outer circle, while duct (160) appears as the inner circle. Lumen (40) running through duct (160) is shown clearly in FIG. 9. It will also be readily apparent that both the duct (160) and the inflation tube (90) are hollow, and that there is no fluid-flow communication possible between the two, as is described in further detail below.

About the outer wall of the catheter (50), is a cluster of balloons (30), being arranged in a substantially circular arrangement. Each of the balloons (30) in the cluster is bonded to each adjoining balloon (30) along a common edge at least partially along the length of each of the balloons (30). It will be appreciated by an expert in the field that the balloons (30) may be bonded using adhesives or using a variety of conventional heat bonding techniques. It is envisioned that in another embodiment (not depicted), each of the balloons (30) in the cluster is held together using ties, tethers or a support structure, or a combination of such ties, adhesives or heat bonding. In addition, the cluster of balloons (30) is also bonded to the surface of the wall of the catheter (50). In a preferred embodiment of the invention, heat bonding is used to achieve that attachment. This bonding prevents dislodgement of the cluster of balloons (30) from the catheter (50) during operation of the device (20).

Each balloon has a barrel portion (100) and, on either side thereof, a cone (140, 170) and a tail (130, 150). For obvious reasons, the tail formation occurring closest to the distal end (70) of the device (20) is referred to as the distal tail (150), while the tail formation occurring closest to the inflating end (60) of the device (20) is referred to as the proximal tail (130). In a most preferred embodiment of the invention, it is the series of proximal tails (130) that are bonded onto the outer wall of the catheter (50).

Figure 2:
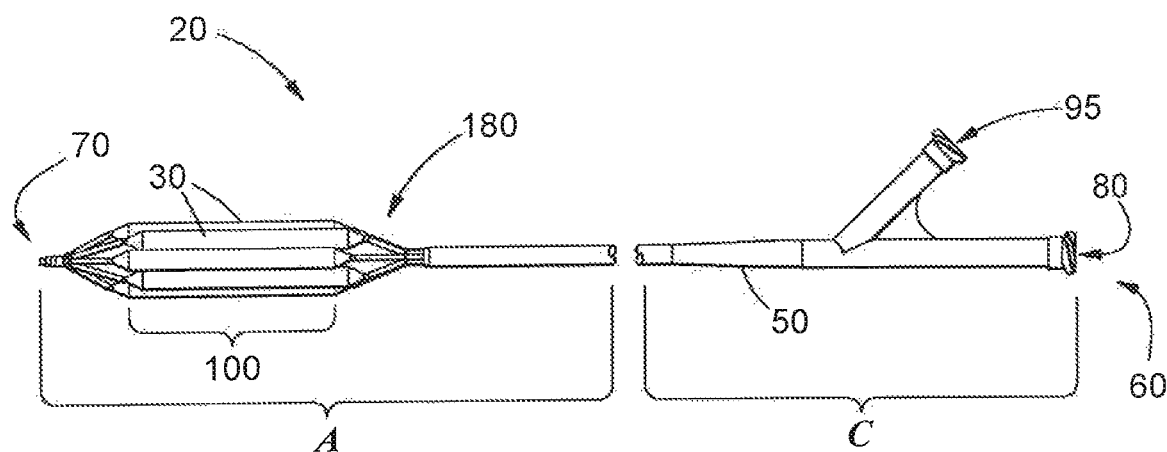
FIG. 2 depicts an isometric view of the device, in its deployed condition, in accordance with a first aspect of the invention.
Figure 3:
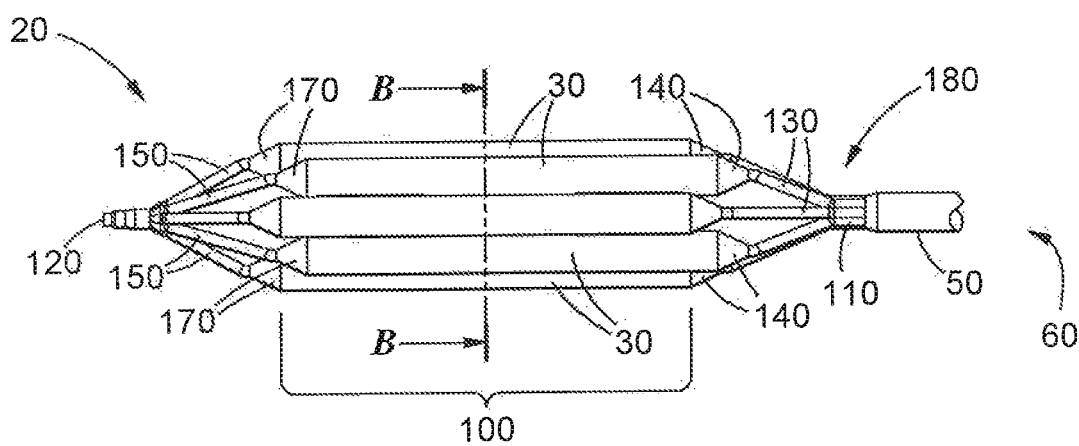
FIG. 3 depicts a side view of the device depicted in FIG. 2 along line A-A.

Each of the series of proximal tails 130 of each balloon (30) is hollow, essentially taking the form of an inflationary tube. It has already been explained how, on one end, each distal tail (150) transitions into a cone (140). At the other end, each proximal tail 150 extends through the catheter (50) and from there at least partially into the inflation tube (90). This occurs at common opening (180) (which is best depicted in FIGS. 2-4). The common opening (180) is sealed to prevent the escape of inflating fluid from the inflation tube (90) into the airway. It is also stressed that the inflation tube (90) is further sealed along its length to prevent the escape of inflating fluid into duct (160).

The series of distal tails (150) terminates in a common distal tip (150), the distal tip (150) sealing the balloon arrangement hermetically, to as to facilitate pressurisation of the cluster on inflation, and to prevent the escape of inflating fluid into the airway.

The cluster of balloons (30) is designed to be manipulated selectively between a stowed condition (best depicted in FIG. 7(b)), in which the balloons (30) are deflated, and a deployed condition, in which the balloons (30) are inflated (best depicted in FIG. 2). In the stowed position depicted, the cluster of balloons (30) is folded and wrapped tightly around the catheter (50). The inflating means is located proximate the inflating end (60) of the catheter (50). In the preferred example depicted in the Figures, the inflating means comprises an inflation port (95), which is designed to be connected to an external source of pressurised fluid (not depicted) for inflating the balloons (30).

In a preferred embodiment of the invention, the device (20) includes a film layer (190), for providing additional support to the cluster of balloons (30). The film layer (190) follows, at least partially, the contours of at least some of the balloons (30) in the cluster. This is best illustrated in FIG. 5. The film layer (190) is also bonded to part of the balloons (30) in the cluster. More specifically, and as will be best observed in FIG. 5, the film layer (190) is bonded to the inner surface of the balloons (30) in the cluster. In the embodiment depicted here, the film layer (190) is bonded to each one of the balloons (30) in the cluster, but it will be appreciated by the expert in the field that this is not absolutely essential in order to achieve the advantages of the invention.

The film layer (190) is made of a material selected from the group consisting of: polyethylene terephthalate, poly (ether-block-amide), polyimide, polyurethane, and a combination of these.

A primary purpose of the film layer (190) is to improve the structural strength of the cluster of balloons (30) while simultaneously not hindering the ability of the balloons (30) to inflate. Furthermore, it is important for catheter (50) performance that the balloons (30) remain in contact with each other when inflated to prevent individual balloons (30) from prolapsing inwardly towards the central axis of the catheter (50) or from expanding radially outwardly. The invention, as described, achieves these outcomes. It will be noted that the devices disclosed in the prior art—even those comprising a film layer—do not include the film layer located on the interior surface of the balloons (30). In fact, in the present invention, the fil, layer (190) is always located on the interior surface of the balloons (30), as is best depicted in FIG. 5. This has been found to achieve a notable advantage over the prior art, namely that it aids in the prevention of a prolapse of the balloons (30) in the cluster.

Balloons (30) are bonded together along their contacting edges using heat bonding processes, alternatively, using an adhesive. The presence of the film layer (190) is advantageous in that it provides additional support and strength to the structure of the cluster of balloons (30). It has also been found to prevent the lumen (40) from being occluded in the event of a prolapsed balloon (30)—which is further advantageous. In a preferred configuration, the film layer (190) has a thickness of between 0.005 mm-0.100 mm, and more preferably between 0.020 mm-0.050 mm.

In the embodiment of the invention that is depicted in the Figures, an eight-balloon configuration is shown. However, this invention requires as few as two balloons (30) to operate, although it will certainly operate (to varying degrees of success) utilising any number of balloons (30). For practical purposes, it has been found that 5-12 balloon clusters are most ideal. In the embodiments of the invention described here, each balloon (30) is envisaged to have a wall thickness of between 8 µm to 60 µm, and preferably between 22 µm to 33 µm—suitable for an adult—and between 10 µm to 20 µm—suitable for a child. It is also envisaged that the wall thickness of any balloon (30) will vary at different points along its length, and be thickest at the tail 140 relative to the barrel portion (100), where it is at its thinnest.

In order to discuss the operation of the device, it is instructive, first, to describe certain components of the device (20). It will be noted (most readily from FIGS. 2 and 6(a)) that each balloon (30) comprises a barrel portion (100) and a proximal cone (140), the cone (140) being connected to a proximal tail (130) which, as has already been described, serves as an inflation tube. Each such inflation tube, extends internally through the inflation tube (90), and is in fluid flow communication with inflating port 95. Typically, that preferred pressurised fluids used for inflation are: sterile water, saline, a contrast medium and a combination of these. It will be appreciated by the expert in the field that, on the introduction of pressurised fluid into the inflation tube (90) via inflationary port 95, and thence into proximal tails 130, balloons (30) will be inflated, thus forcing the airway to dilate, One of the primary advantages of the invention is the fact that, when the cluster of balloons (30) is fully deployed, a channel is formed that permits free flow of fluid—typically air and/or medication—while simultaneously relieving the stricture.

It has already been explained how each of the series of balloons (30) terminates in a distal cone (170) and distal tail (150) on its opposite end. Each distal tail (150), in turn, terminates in a common distal tip (120) at its other end. It will be noted that the inflation system of device (20) is sealed hermetically, from the commencement of each tail 140, along the full length of each balloon (30), through the series of distal balloon tubes 150, and to the distal tip (120). In this way, no inflationary fluid is ever introduced into the lumen (40) or into the airway. In fact, it is also specifically envisaged in other embodiments of the invention (not depicted) that the distal tails 150 will be at least a little smaller than the corresponding proximal tails 130, in an effort to further minimise the total volume of the device (20).

The distal tip (120) is also designed to minimise trauma to tissue during the insertion, operation, and extraction of the device (20).

The proximal tails 130, and the distal tails 150 and distal cones 170 also serve a secondary function of providing structural integrity to the device (20), and help to maintain the integrity of the shape and configuration of the device (20) in the deployed form depicted in the Figures.

Figure 7:
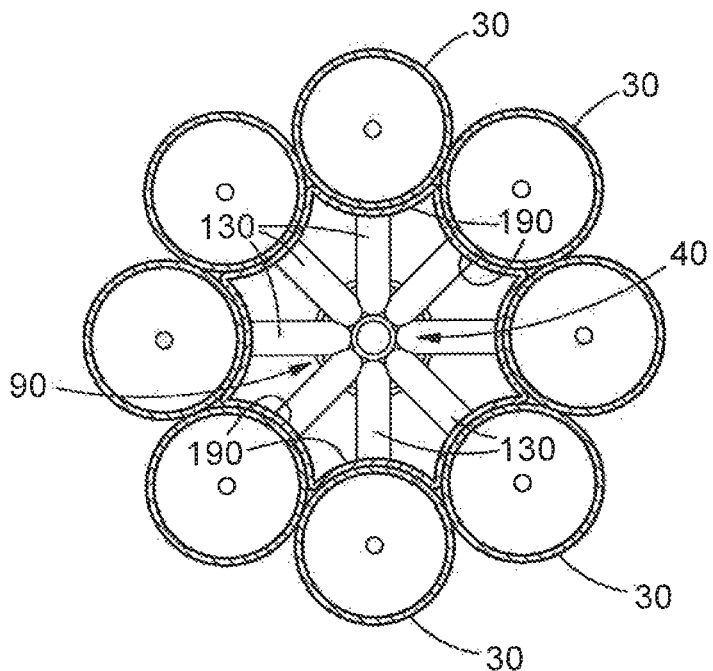
FIG. 7 depicts an axial cross section through the device depicted in FIG. 3, along line B-B, as viewed from the distal tip.
Figure 8A:
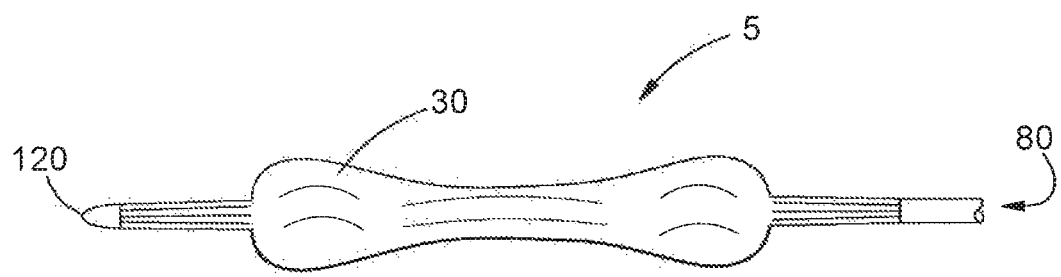
FIG. 8a depicts a comparative cluster of balloons, in isolation, in the stowed state, but not staggered in accordance with the invention.
Figure 8B:
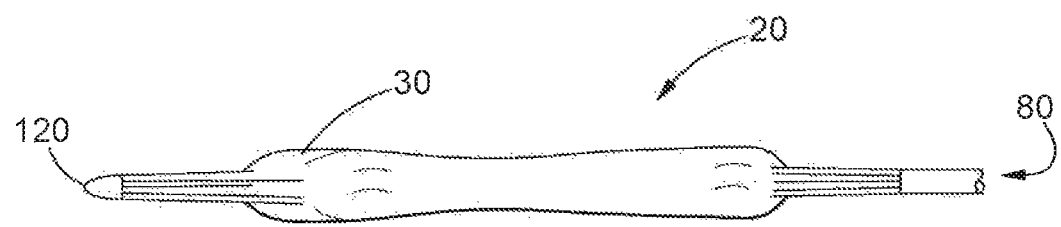
FIG. 8b depicts a cluster of balloons, in isolation, in the stowed state and staggered in accordance with the invention.

One of the key features of the device (20) lies in the fact that, when in the stowed condition, each balloon (30) is folded and staggered relative to each adjacent balloon (30), to prevent a substantial overlay between pairs of balloons, so as to achieve an optimal, smallest diameter of the complete cluster of balloons. More specifically—and critically—it will be noted that the proximal cone (140) and distal cone (170) of any two adjacent balloons (30) never overlap—as such, the cones (140, 170) are always staggered relative to each other. This is because the wall thickness of each balloon (30) is at its thickest at the tail (130, 150) and thinnest at the barrel 100, and the cone (140) is intermediate between the two. Accordingly, by staggering the cones (140, 170), the overall thickness of the device (20) in toto is minimised. This is illustrated in FIG. 7(*a*)—which illustrates a prior art solution (not the invention)—and FIG. 7(*b*). In FIG. 7(*a*), balloons (30) are arranged in the conventional, parallel overlap formation. Conversely, in FIG. 7(*b*), the balloons (30) are staggered to prevent substantial overlay. The difference between the two will be immediately apparent: the packing efficiency achieved by the invention is considerably better than that of the prior art. Simply put: the overall volume occupied by the stowed balloons (30) in the invention is considerably smaller than that achievable by prior art solutions. The staggered arrangement of adjacent balloons (30) is readily apparent from FIG. 3.

In a preferred embodiment of the invention, at least some (and preferably all) of proximal tails 130 are bonded to the catheter (50). Some (and preferably all) of distal tails 150 are bonded to the distal tip (120). This ensures that the balloon (30) cluster is affixed firmly and cannot move except for between the stowed conditions and the deployed condition.

Also in a preferred embodiment, each balloon (30) includes a central barrel portion (100) so that, when the balloon (30) is in a deployed condition, the barrel portion is circular in cross-section. It will be appreciated by the expert in the field that numerous embodiments are possible in which the balloon assumes other shapes in cross-section, and that this element is not core to the invention—one such embodiment that is specifically conceived is the so-called hourglass shape inflationary balloon. None of those other embodiments is depicted here.

The device (20) further comprises a secondary port (80), opening into the duct (160), for insufflation of a medicament (not depicted)—simply put: secondary port (80) is continuous with, and in direct fluid flow communication with, duct (160). What makes this possible is the fact that duct (160) is open at the distal end (70) of catheter 20, thus facilitating targeted release of the medicament, via lumen (40). Typically, such medicaments would include: air, oxygen, anaesthesia, topical drugs, and a combination of these.

The secondary port (80) is further envisaged to be used to provide jet insufflation of oxygen, alternatively to facilitate manoeuvring of a laser fibre (not depicted) through the airway into position. This is extremely convenient for the attending medical staff, particularly when attempting to manoeuvre equipment in spaces as confined as an (already) constricted airway.

For this purpose, conveniently, duct (160) is dimensioned and configured to facilitate manoeuvring of a secondary medical tool (not depicted) therethrough. Typically, such secondary medical tools would include: a guidewire, a laser fibre, a tracheal stent, and a combination of these.

It will be appreciated by the expert in the field—crucially—that the use of the secondary port 190 to introduce medicaments and/or manoeuvre secondary medical tools is conducted entirely independently of achieving inflation of the cluster of balloons (30). This is another of the key features of the invention, namely: that use of device (20) permits continuous ventilation of a patient, even when the balloons (30) are in their deployed condition—the device (20) need not be retracted in order to achieve ventilation or medication of a patient. This represents a major advance over prior art dilators.

In order to achieve the same result (of the introduction of a medicament using the device (20)), although in a different way, in another preferred embodiment of the invention (not depicted), at least some of the balloons (30) are coated in a medicinal compound, the medicinal compound being dispersed on inflation of the balloons (30).

It will also be appreciated by the expert in the field that achieving balloon (30) dilation of a threatened airway, using the device (20) described here, obviates the need for urgent surgical intervention and avoids an immediate tracheotomy or stenting of the trachea. This allows for better medical decision making to choose the correct long-term management of the threatened airway—either by repeat dilations or a tracheal resection (without the rest of the trachea damaged by the surgical intervention which would make the 'damaged trachea' segment longer).

The catheter (50) is dimensioned and configured for insertion and delivery in and through a conventional rigid bronchoscope, alternatively a conventional laryngoscope (not depicted). It is also envisaged that, in other embodiments of the invention, other manoeuvring devices (not depicted) may be preferred for achieving insertion and delivery. This assists in the process of introducing the device (20) in vivo to the site of constriction in the airway.

Also in a preferred embodiment of the invention, a visual indicator (110) is included within in the cluster of balloons (30). This indicator 110, which essentially takes the form of a marker, is used to indicate the position of the cluster of balloons (30) under direct inspection by the medical practitioner operating the device (20). In an alternative embodiment of the invention (not depicted) the indicator 110 is designed to be observed under x-ray inspection. This is particularly helpful in achieving precision in deploying the balloons (30) optimally into the site of constriction.

In yet another embodiment of the invention (not depicted), device (20) further includes a check-valve (not depicted) for dissipating excess pressure. The check-valve, in turn, comprises a stopper and spring arrangement, the spring being biased towards a loaded position in which the stopper is held fast, and characterised in that the spring is movable towards a sprung condition, when the fluid pressure within the inflation tube (90) exceeds a predetermined value, thus forcing the stopper to open, and vent the fluid.

Each balloon (30) is capable of achieving substantially complete inflation at pressures of between 4 bar to 16 bar, and preferably between 6 bar to 14 bar. However, it will be appreciated that in some embodiments of the invention, pressures may, in fact, be increased to as much as 24 bar, if necessary, to dilate a constricted airway. In order to withstand such pressures, without causing a (partial) collapse of duct (160), the duct (160) is reinforced, such as with braiding, in order to provide the required structural integrity.

Purely for completeness, and separate to the invention as claimed, it is mentioned that device (20) is retrieved from the body, preferably, in a process that is essentially a reversal of the insertion process. It commences with the operator (not depicted) applying a vacuum at the inflating end (60)—essentially, voiding all the inflating fluid from the cluster of balloons (30). The shape and configuration of the balloons (30) will automatically cause the cluster to reassume (at least substantially) its initial folded condition.

Once this is achieved, it remains a simple matter to reverse the catheter (50) out of the airway and through the bronchoscope, alternatively laryngoscope, through which it was deployed initially. In other embodiments, not depicted, it is also envisaged that an endotracheal tube, alternatively a tracheostomy tube, further alternatively a supraglottic airway device, nasopharyngeal tube or laryngeal mask airway would serve as a manoeuvring guide. It is also envisaged, particularly in emergency cases, that the catheter (50) will be inserted directly into the airway—the use of a bronchoscope or laryngoscope is not always strictly necessary, though it is certainly preferable. In another embodiment of the invention, a seal is provided in order to seal the device (20) against the manoeuvring guide or the airway or the mouth to prevent fluid escaping in the spaces between the catheter (50) and the manoeuvring guide, airway or mouth.

It will be appreciated that numerous embodiments of the invention could be performed without departing from the scope of the invention as defined in the claims.

The invention claimed is:

1. An airway dilation device comprising:
   a catheter, being dimensioned and configured for insertion at least partially into an airway, the catheter having an inflating end, and a distal end;
   a continuous inflation tube, being housed substantially concentrically within the catheter, the inflation tube having a lumen defined by its inner wall, and terminating in the same inflating end as the catheter;
   a duct, for the insufflation of a fluid, the duct also being housed substantially concentrically within the catheter, and bounded by the inflation tube along at least some of the length thereof, the duct being sealed hermetically against any fluid flow communication between it and the inflation tube;
   a cluster of balloons, arranged in a substantially circular arrangement about wall of the catheter, the balloons being manipulated selectively between a stowed condition, in which the balloons are deflated, and a deployed condition, in which the balloons are inflated, and wherein each balloon further includes a proximal cone and a proximal tail formation on a proximal end of each respective balloon, and wherein each balloon further includes a distal cone and a distal tail on a distal end of each respective balloon; and
   inflating means, for inflating the balloons;
   characterised, first, in that, when in the stowed condition, each balloon is folded and staggered relative to each adjacent balloon, to prevent a substantial overlay between each pair of adjacent balloons, so as to achieve an optimal, smallest diameter of the complete cluster of balloons and characterised, second, in that continuous insufflation remains possible, even when the balloons are in their deployed condition;
   wherein each proximal tail extend through a common opening into the inflation tube, the common opening being sealed to prevent the escape of inflating fluid into the duct, alternatively into the airway, further alternatively into both the duct and the airway.

2. A device according to claim 1 wherein each balloon is bonded to each adjoining balloon in the cluster, along at least one edge.

3. A device according to claim 1, wherein the cluster of balloons is affixed securely to the wall of the catheter, along at least some portion thereof, and held fast, so as to prevent separation of the cluster from the catheter.

4. A device according to claim 3, wherein each distal tail is affixed securely to the wall of the catheter, along at least some portion thereof, and held fast, so as to restrict movement of the balloons to positioning between the stowed condition and the deployed condition only.

5. A device according to claim 3, wherein each of the proximal tails of each balloon takes the form of an inflationary tube for its associated balloon.

6. A device according to claim 1 wherein the device further includes a film layer for providing additional support to the cluster of balloons.

7. A device according to claim 6, wherein the film layer follows, at least partially, the contours of at least some of the balloons in the cluster.

8. A device according to claim 6, wherein the film layer is bonded to at least part of at least some of the balloons in the cluster.

9. A device according to claim 8, wherein the film layer is bonded to the inner surface of the balloons.

10. A device according to claim 6, wherein the film layer is made of a material selected from the group consisting of: polyethylene terephthalate, poly(ether-block-amide), polyamide, polyurethane, and a combination of these.

11. A device according to claim 1, wherein the distal tails of each balloon terminates in a common distal tip, the distal tip sealing the balloon arrangement hermetically, to as to facilitate pressurisation of the cluster on inflation, and to prevent the escape of inflating fluid into the airway.

12. A device according to claim 4, wherein the proximal cone and the distal cone of any two adjacent balloons are arranged relative to each other so as never to overlap, thus ensuring that any one balloon is staggered relative to each adjacent balloon.

13. A device according to claim 1, wherein each balloon includes a central barrel portion, characterised in that, when the balloon is in a deployed condition, the barrel portion is substantially circular in cross-section.

14. A device according to claim 1, wherein the inflating means comprises an inflating port located on the catheter, characterised in that the inflating port is dimensioned and configured to engage an external source of pressurised fluid for inflating the balloons, the inflationary port being in fluid flow communication with each proximal tail.

15. A device according to claim 1, wherein the device further comprises a secondary port, located at the inflating end of the catheter, alternatively along the length of the catheter, characterised in that the secondary port opens into the duct, for insufflation of a medicament.

16. A device according to claim 15, wherein the medicament is selected from the group consisting of: air, oxygen, anaesthesia, topical drugs, and a combination of these.

17. A device according to claim 15, wherein the secondary port is used to provide jet insufflation of oxygen.

18. A device according to claim 15, characterised in that the duct is dimensioned and configured to facilitate manoeuvring of a secondary medical tool therethrough.

19. A device according to claim 15, wherein the secondary medical tool is selected from the group consisting of: a guidewire, a laser fibre, a tracheal stent, and a combination of these.

20. A device according to claim 1, characterised in that the catheter is dimensioned and configured for insertion and delivery in and through a device selected from the group consisting of: a conventional rigid bronchoscope, a conventional laryngoscope, an endotracheal tube, a tracheostomy tube, supraglottic airway device, nasopharyngeal tube and laryngeal mask airway.

21. A device according to claim 1, wherein at least some balloons are coated in a medicinal compound, characterised in that the medicinal compound is dispersed on inflation of the balloons.

22. A device according to claim 1, wherein the device further comprises at least one visual indicator, for indicating the position of the cluster under direct inspection, alternatively under x-ray inspection.

23. A device according to claim 1, wherein the check-valve comprises a stopper and spring arrangement, the spring being biased towards a loaded position in which the stopper is held fast, and characterised in that the spring is movable towards a sprung condition, when the fluid pressure within the lumen exceeds a predetermined value, thus forcing the stopper to open, and vent the fluid.

24. A device according to claim 1, wherein each balloon has a wall thickness of between 8 µm to 60 µm.

25. A device according to claim 13, wherein the wall thickness of any balloon varies at different points along its length, characterised in that the wall thickness of a balloon is relatively thicker on either cone and tail, and at its thinnest in the barrel portion.

26. A device according to claim 1, wherein each balloon is capable of maintaining substantially complete inflation at pressures of between 4 bar to 24 bar.

27. A device according to claim 26, wherein each balloon is capable of maintaining substantially complete inflation at pressures of between 6 bar to 14 bar.

28. A device according to claim 26, wherein the inflating fluid is selected from the group consisting of: air, sterile water, saline, a contrast medium fluid, and a combination of these.

29. An airway dilation device comprising:
a catheter, being dimensioned and configured for insertion at least partially into an airway, the catheter having an inflating end, and a distal end;
a continuous inflation tube, being housed substantially concentrically within the catheter, the inflation tube having a lumen defined by its inner wall, and terminating in the same inflating end as the catheter;
a duct, for the insufflation of a fluid, the duct also being housed substantially concentrically within the catheter, and bounded by the inflation tube along at least some of the length thereof, the duct being sealed hermetically against any fluid flow communication between it and the inflation tube;
a cluster of balloons, arranged in a substantially circular arrangement about wall of the catheter, the balloons being manipulated selectively between a stowed condition, in which the balloons are deflated, and a deployed condition, in which the balloons are inflated, and wherein each balloon further includes a proximal cone and a proximal tail formation on a proximal end of each respective balloon, and wherein each balloon further includes a distal cone and a distal tail on a distal end of each respective balloon; and
inflating means, for inflating the balloons;
characterised, first, in that, when in the stowed condition, each balloon is folded and staggered relative to each adjacent balloon, to prevent a substantial overlay between each pair of adjacent balloons, so as to achieve an optimal, smallest diameter of the complete cluster of balloons and characterised, second, in that continuous insufflation remains possible, even when the balloons are in their deployed condition
wherein the distal tails of each balloon terminates in a common distal tip, the distal tip sealing the balloon arrangement hermetically, to as to facilitate pressurisation of the cluster on inflation, and to prevent the escape of inflating fluid into the airway.

30. A device according to claim 29, wherein the cluster of balloons is affixed securely to the wall of the catheter, along at least some portion thereof, and held fast, so as to prevent separation of the cluster from the catheter; wherein
each distal tail is affixed securely to the wall of the catheter, along at least some portion thereof, and held fast, so as to restrict movement of the balloons to positioning between the stowed condition and the deployed condition only.

31. A device according to claim 29, characterised in that the catheter is dimensioned and configured for insertion and delivery in and through a device selected from the group consisting of: a conventional rigid bronchoscope, a conventional laryngoscope, an endotracheal tube, a tracheostomy tube, supraglottic airway device, nasopharyngeal tube and laryngeal mask airway.

32. A device according to claim 29, wherein the device further includes a film layer for providing additional support to the cluster of balloons, wherein
the film layer follows, at least partially, the contours of at least some of the balloons in the cluster, alternatively
the film layer is bonded to at least part of at least some of the balloons in the cluster.

33. A device according to claim 29, wherein the inflating means comprises an inflating port located on the catheter, characterised in that the inflating port is dimensioned and configured to engage an external source of pressurised fluid for inflating the balloons, the inflationary port being in fluid flow communication with each proximal tail.

34. A device according to claim 29, wherein the device further comprises a secondary port, located at the inflating end of the catheter, alternatively along the length of the catheter, characterised in that the secondary port opens into the duct, for insufflation of a medicament; wherein
the secondary port is used to provide jet insufflation of oxygen.

35. A device according to claim 34, characterised in that the duct is dimensioned and configured to facilitate manoeuvring of a secondary medical tool therethrough; wherein
the secondary medical tool is selected from the group consisting of: a guidewire, a laser fibre, a tracheal stent, and a combination of these.

36. A device according to claim 29, wherein each balloon includes a central barrel portion, characterised in that, when the balloon is in a deployed condition, the barrel portion is substantially circular in cross-section; wherein
the wall thickness of any balloon varies at different points along its length, characterised in that the wall thickness of a balloon is relatively thicker on either cone and tail, and at its thinnest in the barrel portion.

37. A device according to claim 29, wherein at least some balloons are coated in a medicinal compound, characterised in that the medicinal compound is dispersed on inflation of the balloons.

38. A device according to claim 29, wherein the check-valve comprises a stopper and a spring, the spring being biased towards a loaded position in which the stopper is held fast, and characterised in that the spring is movable towards a sprung condition, when the fluid pressure within the lumen exceeds a predetermined value, thus forcing the stopper to open, and vent the fluid.

\* \* \* \* \*